United States Patent [19]
Dean et al.

[11] Patent Number: 5,888,474
[45] Date of Patent: Mar. 30, 1999

[54] TECHNETIUM-99M LABELED PEPTIDES FOR GPIIB/IIIA LIGANDS USEFUL FOR THROMBUS IMAGING

[75] Inventors: Richard T. Dean; John Lister-James, both of Bedford, N.H.

[73] Assignee: Diatide, Inc., Londonderry, N.H.

[21] Appl. No.: 478,725

[22] Filed: Jun. 7, 1995

Related U.S. Application Data

[60] Division of Ser. No. 273,274, Jul. 11, 1994, and a continuation-in-part of Ser. No. 480,551, Jun. 7, 1995, and a continuation-in-part of Ser. No. 807,062, Nov. 27, 1991, Pat. No. 5,443,815, said Ser. No. 273,274, is a continuation of Ser. No. 886,752, May 20, 1992, abandoned, said Ser. No. 480,551, is a continuation of Ser. No. 264,176, Jun. 22, 1974, abandoned, which is a continuation of Ser. No. 653,012, Feb. 8, 1991, abandoned.

[51] Int. Cl.[6] .......................... A61K 51/00; A61M 36/14
[52] U.S. Cl. ...................... 424/1.69; 424/1.11; 424/1.65; 534/14; 530/300
[58] Field of Search ................... 424/1.11, 1.65, 424/1.69, 9.1, 9.3, 9.4, 9.5; 206/223, 569, 570; 534/7, 10–16; 530/300, 324–330, 333, 334, 338, 317, 311

[56] References Cited

U.S. PATENT DOCUMENTS

| | | | |
|---|---|---|---|
| 5,095,111 | 3/1992 | Lever et al. | 540/544 |
| 5,180,816 | 1/1993 | Dean | 530/404 |
| 5,217,705 | 6/1993 | Reno et al. | 424/1.11 |
| 5,225,180 | 7/1993 | Dean et al. | 424/1.11 |
| 5,382,654 | 1/1995 | Lyle et al. | 530/311 |
| 5,395,609 | 3/1995 | Stuttle | 424/1.69 |
| 5,443,815 | 8/1995 | Dean et al. | 424/1.41 |
| 5,443,816 | 8/1995 | Zamora et al. | 424/1.69 |
| 5,508,020 | 4/1996 | Dean et al. | 424/1.69 |
| 5,552,525 | 9/1996 | Dean | 530/326 |
| 5,567,408 | 10/1996 | Zamora | 424/1.69 |
| 5,672,585 | 9/1997 | Pierschbacher et al. | 514/11 |
| 5,736,122 | 4/1998 | Dean et al. | 424/1.69 |
| 5,780,303 | 7/1998 | Pierschbacher et al. | 436/10 |

FOREIGN PATENT DOCUMENTS

| | | |
|---|---|---|
| 9321962 | 11/1993 | WIPO . |
| 9323085 | 11/1993 | WIPO . |

*Primary Examiner*—Jose' G. Dees
*Assistant Examiner*—Dameron Jones
*Attorney, Agent, or Firm*—Patricia A. McDaniels; Kevin E. Noonan

[57] ABSTRACT

This invention relates to radiolabeled peptides and methods for producing such peptides. Specifically, the invention relates to specific binding peptides, methods and kits for making such peptides, and methods for using such peptides labeled with technetium-99m via a radiolabel-binding moiety covalently linked to the peptide to image thrombus sites in a mammalian body.

10 Claims, No Drawings

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( i x ) FEATURE:
  ( A ) NAME/KEY: Cross-links
  ( B ) LOCATION: 1..5
  ( D ) OTHER INFORMATION: /label= thioether
    / note= "The sidechain sulfur of the C-terminal
    cysteine residue is covalently linked as an ether
    to the group [CH2CO], which group forms an amide ( x i ) SEQUENCE DESCRIPTION: SEQ ID NO:1:

Tyr  Arg  Gly  Asp  Cys
1                    5

( 2 ) INFORMATION FOR SEQ ID NO:2:

( i ) SEQUENCE CHARACTERISTICS:
    ( A ) LENGTH: 8 amino acids
    ( B ) TYPE: amino acid
    ( D ) TOPOLOGY: circular ( i i ) MOLECULE TYPE: peptide ( i x ) FEATURE:
    ( A ) NAME/KEY: Cross-links
    ( B ) LOCATION: 1..5
    ( D ) OTHER INFORMATION: /label= thioether
      / note= "The sidechain sulfur atom of the cysteine
      residue is covalently linked to the group [CH2CO],
      which group forms an amide bond with the ( x i ) SEQUENCE DESCRIPTION: SEQ ID NO:2:

Tyr  Arg  Gly  Asp  Cys  Trp  Gly  Gly
1                    5

( 2 ) INFORMATION FOR SEQ ID NO:3:

( i ) SEQUENCE CHARACTERISTICS:
    ( A ) LENGTH: 7 amino acids
    ( B ) TYPE: amino acid
    ( D ) TOPOLOGY: circular ( i i ) MOLECULE TYPE: peptide ( i x ) FEATURE:
    ( A ) NAME/KEY: Cross-links
    ( B ) LOCATION: 1..5
    ( D ) OTHER INFORMATION: /label= thioether
      / note= "The sidechain sulfur atom of the cysteine
      residue is covalently linked to the group [CH2CO]
      to form a thioether, and the [CH2CO]group is ( x i ) SEQUENCE DESCRIPTION: SEQ ID NO:3:

Tyr  Arg  Gly  Asp  Cys  Phe  Gly
1                    5

( 2 ) INFORMATION FOR SEQ ID NO:4:

( i ) SEQUENCE CHARACTERISTICS:
    ( A ) LENGTH: 8 amino acids
    ( B ) TYPE: amino acid
    ( D ) TOPOLOGY: circular ( i i ) MOLECULE TYPE: peptide ( i x ) FEATURE:
    ( A ) NAME/KEY: Cross-links
    ( B ) LOCATION: 1..5

-continued (D) OTHER INFORMATION: /label= thioether
                / note= "The sidechain sulfur atom of the cysteine
                is covalently linked to the group [CH2CO]to form
                a thioether; the [CH2CO]group is further linked (xi) SEQUENCE DESCRIPTION: SEQ ID NO:4:

Tyr  Arg  Gly  Asp  Cys  Gly  Gly  Gly
1                    5

(2) INFORMATION FOR SEQ ID NO:5:

(i) SEQUENCE CHARACTERISTICS:
            (A) LENGTH: 7 amino acids
            (B) TYPE: amino acid
            (D) TOPOLOGY: circular (ii) MOLECULE TYPE: peptide (ix) FEATURE:
            (A) NAME/KEY: Cross-links
            (B) LOCATION: 1..5
            (D) OTHER INFORMATION: /label= thioether
                / note= "The sidechain sulfur atom of the cysteine
                is covalently linked to the group [CH2CO]to form
                a thioether; said group is further covalently (xi) SEQUENCE DESCRIPTION: SEQ ID NO:5:

Tyr  Arg  Gly  Asp  Cys  Gly  Gly
1                    5

(2) INFORMATION FOR SEQ ID NO:6:

(i) SEQUENCE CHARACTERISTICS:
            (A) LENGTH: 8 amino acids
            (B) TYPE: amino acid
            (D) TOPOLOGY: circular (ii) MOLECULE TYPE: peptide (ix) FEATURE:
            (A) NAME/KEY: Cross-links
            (B) LOCATION: 1
            (D) OTHER INFORMATION: /label= thioether
                / note= "The sulfur in the first cysteine is
                covalently linked to a [3-aminopropyl group; the
                sulfur of the second cysteine is linked to a (xi) SEQUENCE DESCRIPTION: SEQ ID NO:6:

Tyr  Cys  Gly  Asp  Cys  Gly  Gly  Gly
1                    5

(2) INFORMATION FOR SEQ ID NO:7:

(i) SEQUENCE CHARACTERISTICS:
            (A) LENGTH: 8 amino acids
            (B) TYPE: amino acid
            (D) TOPOLOGY: circular (ii) MOLECULE TYPE: peptide (ix) FEATURE:
            (A) NAME/KEY: Cross-links
            (B) LOCATION: 1..5
            (D) OTHER INFORMATION: /label= thioether
                / note= "The sidechain sulfur atom of the cysteine
                is covalently linked to the group [CH2CO]to form
                a thioether; this group then forms an amide bond (xi) SEQUENCE DESCRIPTION: SEQ ID NO:7:

Tyr  Lys  Gly  Asp  Cys  Gly  Gly  Gly
1                    5

-continued ( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: circular ( i i ) MOLECULE TYPE: peptide ( i x ) FEATURE:
        ( A ) NAME/KEY: Disulfide-bond
        ( B ) LOCATION: 3..9
        ( D ) OTHER INFORMATION: /label= Apc
            / note= "The sidechain sulfur of the cysteine
            residue at position 6 is covalently linked to a
            [ 3- aminopropyl]group and hence is blocked"

( x i ) SEQUENCE DESCRIPTION: SEQ ID NO:8:

```
Gly Gly Cys Asn Pro Cys Gly Asp Cys
1               5
```

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Gly Gly Arg Gly Asp Ser
1               5
```

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Gly Gly Arg Gly Asp Gly Gly Arg Gly Asp Ser
1               5                   1 0
```

( 2 ) INFORMATION FOR SEQ ID NO:11:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Gly Gly Arg Gly Asp Gly Gly Arg Gly Asp Gly Gly Arg Gly Asp Ser
1               5                   1 0                 1 5
```

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Lys Arg Ala Arg Gly Asp Asp Met Asp Asp Tyr
```

(2) INFORMATION FOR SEQ ID NO:13:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:13:

```
Arg Arg Arg Arg Arg Arg Arg Arg Arg Gly Asp
1               5                   10
```

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:14:

```
Gly Arg Gly Asp Val Lys
1               5
```

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:15:

```
Gly Arg Gly Asp Val
1               5
```

(2) INFORMATION FOR SEQ ID NO:16:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:16:

```
Gly Arg Gly Asp Val Arg Gly Asp Phe Lys
1               5                   10
```

(2) INFORMATION FOR SEQ ID NO:17:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:17:

```
Gly Arg Gly Asp Val Arg Gly Asp Phe
1               5
```

(2) INFORMATION FOR SEQ ID NO:18:

( i ) SEQUENCE CHARACTERISTICS:
 ( A ) LENGTH: 7 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:18:

Gly Gly Gly Arg Gly Asp Phe
1               5

( 2 ) INFORMATION FOR SEQ ID NO:19:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 3
  ( D ) OTHER INFORMATION: /label= Apc
   / note= "The sidechain sulfur of the cysteine
   residue is covalently linked to a [3-aminopropyl]
   group forming a thioether"

( x i ) SEQUENCE DESCRIPTION: SEQ ID NO:19:

Asn Pro Cys Gly Asp
1               5

( 2 ) INFORMATION FOR SEQ ID NO:20:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:20:

Gly Arg Gly Asp Gly Gly
1               5

( 2 ) INFORMATION FOR SEQ ID NO:21:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:21:

Gly Gly Arg Gly Asp Phe
1               5

( 2 ) INFORMATION FOR SEQ ID NO:22:

( i ) SEQUENCE CHARACTERISTICS:
  ( A ) LENGTH: 7 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:22:

Gly Gly Gly Arg Gly Asp Phe
1               5

( 2 ) INFORMATION FOR SEQ ID NO:23:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Gly Arg Gly Asp Gly Gly Gly Gly
1                          5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Gly Arg Gly Asp Gly Gly
1                  5

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

Gly Gly Arg Gly Asp Phe
1                  5

( 2 ) INFORMATION FOR SEQ ID NO:26:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

Gly Gly Gly Arg Gly Asp Phe
1                      5

( 2 ) INFORMATION FOR SEQ ID NO:27:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= Apc
            / note= "The sidechain sulfur atom is covalently
            linked to a [3-aminopropyl]group to form a
            thioether"

( i x ) FEATURE:
        ( A ) NAME/KEY: Modified-site (B) LOCATION: 6
(D) OTHER INFORMATION: /label= Apc
/ note= "The sidechain sulfur atom is covalently
linked to a [3-aminopropyl]group to form a
thioether"

(ix) FEATURE:
(A) NAME/KEY: Modified-site
(B) LOCATION: 10
(D) OTHER INFORMATION: /label= Amide
/ note= "The carboxyl terminus is modified to an
amide"

(xi) SEQUENCE DESCRIPTION: SEQ ID NO:27:

Gly Cys Gly Asp Val Cys Gly Asp Phe Lys
1               5                   10

(2) INFORMATION FOR SEQ ID NO:28:

(i) SEQUENCE CHARACTERISTICS:
(A) LENGTH: 9 amino acids
(B) TYPE: amino acid
(D) TOPOLOGY: linear (ii) MOLECULE TYPE: peptide (ix) FEATURE:
(A) NAME/KEY: Modified-site
(B) LOCATION: 9
(D) OTHER INFORMATION: /label= S- maleimido
/ note= "The sidechain sulfur atom is covalently
linked to a [S-maleimido]group; 3 such peptides
are covalently linked to a nitrogen atom to form a (xi) SEQUENCE DESCRIPTION: SEQ ID NO:28:

Ser Tyr Asn Arg Gly Asp Ser Thr Cys
1               5

(2) INFORMATION FOR SEQ ID NO:29:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO:29:

Asn Asp Gly Asp Phe Glu Glu Ile Pro Glu Glu Tyr Leu Gln
1               5                   10

(2) INFORMATION FOR SEQ ID NO:30:

(i) SEQUENCE CHARACTERISTICS:
(A) LENGTH: 22 amino acids
(B) TYPE: amino acid
(D) TOPOLOGY: linear (ii) MOLECULE TYPE: peptide (ix) FEATURE:
(A) NAME/KEY: Modified-site
(B) LOCATION: 3
(D) OTHER INFORMATION: /label= D- Phe
/ note= "This residue is the D stereoisomer"

(xi) SEQUENCE DESCRIPTION: SEQ ID NO:30:

Gly Gly Phe Pro Arg Pro Gly Gly Gly Gly Asn Gly Asp Phe Glu Glu
1               5                   10                  15
Ile Pro Glu Glu Tyr Leu
                20

( 2 ) INFORMATION FOR SEQ ID NO:31:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /label= D- Phe
            / note= "This residue is the D stereoisomer"

( x i ) SEQUENCE DESCRIPTION: SEQ ID NO:31:

| Gly | Gly | Gly | Phe | Pro | Arg | Pro | Gly | Gly | Gly | Gly | Asn | Gly | Asp | Phe | Glu |
|---|---|---|---|---|---|---|---|---|---|---|---|---|---|---|---|
| 1 | | | | 5 | | | | | 10 | | | | | 15 | |

| Glu | Ile | Pro | Glu | Glu | Tyr | Leu |
|---|---|---|---|---|---|---|
| | | | 20 | | | |

( 2 ) INFORMATION FOR SEQ ID NO:32:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /label= D- Phe
            / note= "This residue is the D stereoisomer"

( i x ) FEATURE:
        ( A ) NAME/KEY: Modified-site
        ( B ) LOCATION: 7
        ( D ) OTHER INFORMATION: /label=Amide
            / note= "The carboxyl terminus is modified to an
            amide"

( x i ) SEQUENCE DESCRIPTION: SEQ ID NO:32:

| Gly | Gly | Phe | Pro | Arg | Pro | Gly |
|---|---|---|---|---|---|---|
| 1 | | | | 5 | | |

( 2 ) INFORMATION FOR SEQ ID NO:33:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Acm
            / note= "This cysteine residue is blocked at the
            sidechain sulfur by covalent linkage to an
            acetamido group"

( i x ) FEATURE:
        ( A ) NAME/KEY: Modified-site
        ( B ) LOCATION: 7
        ( D ) OTHER INFORMATION: /label=Acm
            / note= "This cysteine residue is blocked at the
            sidechain sulfur atom by covalent linkage to an
            acetamido group"

( i x ) FEATURE:
        ( A ) NAME/KEY: Modified-site (B) LOCATION: 8
(D) OTHER INFORMATION: /label= S- maleimido
    / note= "The sidechain sulfur atom of this cysteine
    residue is covalently linked to an [S-maleimido]
    group; 3 such peptides are linked via this group"

(xi) SEQUENCE DESCRIPTION: SEQ ID NO:33:

Gly Pro Arg Pro Cys Gly Cys Cys
1               5

TECHNETIUM-99M LABELED PEPTIDES FOR GPIIB/IIIA LIGANDS USEFUL FOR THROMBUS IMAGING

This application is a divisional of allowed U.S. application Ser. No. 08/273,274, filed Jul. 11, 1994, which is a continuation of U.S. application Ser. No. 07/886,752, filed May 20, 1992 and now abandoned. This application is also a continuation-in-part of allowed U.S. application Ser. No. 08/480,551, filed Jun. 7, 1995, which is a continuation of U.S. application Ser. No. 08/264,176, filed Jun. 22, 1994 and now abandoned, which is a continuation of U.S. application Ser. No. 07/653,012, filed Feb. 8, 1991 and now abandoned. This application is also a continuation-in-part of U.S. application Ser. No. 07/807,062, filed Nov. 27, 1991 and now U.S. Pat. No. 5,443,815, which issued on Aug. 22, 1995.

BACKGROUND OF THE INVENTION

1. Field of the Invention

This invention relates to radiodiagnostic reagents and peptides, and methods for producing labeled radiodiagnostic agents. Specifically, the invention relates to peptides that can be labeled with technetium-99m (Tc-99m), methods and kits for making and radiolabeling such peptides, and methods for using such peptides to image sites of thrombus formation in a mammalian body.

2. Description of the Prior Art

Thrombosis and thromboembolism, in particular deep vein thrombosis (DVT) and pulmonary embolism (PE), are common clinical conditions that are associated with significant morbidity and mortality. It has been estimated that in the U.S. approximately 5 million patients experience one or more episodes of DVT per year and that over 500,000 cases of pulmonary embolism occur, resulting in 100,000 deaths (J. Seabold, Society of Nuclear Medicine Annual Meeting 1990). It has also been estimated that over 90% of all pulmonary emboli arise from DVT in the lower extremities. Anticoagulant therapy can effectively treat these conditions if applied early enough. However, such treatment is associated with risks (e.g. internal bleeding) that prevent unnecessary prophylactic application. More advanced techniques of thrombolytic intervention (such as the administration of recombinant tissue plasminogen activator or streptokinase) can be used in acute cases, but these techniques carry even greater risk. Moreover, effective clinical application of these techniques requires that the site of the offending thrombus be identified so as to monitor the effect of treatment.

For these reasons, a rapid means of localizing thrombi in vivo, most preferably using non-invasive methods, is highly desirable. Methods currently utilized for the identification of thrombolytic sites are contrast venography and compression B-mode ultrasound; the choice of which technique is used depends on the expected location of the thrombus. However the former technique is invasive and both techniques are uncomfortable for the patient. In addition, these methods are in many cases either unsuitable or yield inaccurate results.

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site.

A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. Tc-99m is a preferred radionuclide because it emits gamma radiation at 140 keV, it has a physical half-life of 6 hours, and it is readily available on-site using a molybdenum-99/technetium-99m generator.

A gamma-emitting radiotracer that binds specifically to a component of a thrombus in preference to other tissue when administered in vivo can provide an external scintigraphic image which defines the location of the thrombus-bound radiotracer and hence the thrombus. There are several potential radiotracer targets in thrombi. Thrombi are constructs of blood cells, largely platelets, enmeshed in cross-linked fibrin. Venous thrombi are fibrin-rich, whereas arterial thrombi are platelet-rich. Fibrin and platelets are thus obvious targets for designing radiopharmaceuticals for imaging thrombi, each having multiple possible target sites.

Activated platelets and fibrin have been used as targets in radioimaging thrombi because neither are normally found in circulating blood; circulating blood contains unactivated platelets and fibrinogen, a fibrin precursor. Thrombus formation involves the proteolytic conversion of fibrinogen to fibrin and the physiological conversion of unactivated platelets to an activated state. Since little fibrin circulates in the blood stream (in contrast to its precursor, fibrinogen) and since most circulating platelets are unactivated, fibrin and activated platelets are excellent and specific targets for imaging thrombi because they will not be found to any substantial extent anywhere in vivo other than in a thrombus.

The use of radiolabeled fibrinogen and radiolabeled platelets for radioimaging has a number of disadvantages, however. Blood and background tissue clearance of radiolabeled fibrinogen and platelets are slow, which necessitates a long delay between injection and imaging. Also, as thrombi age radiolabeled platelets become less efficient imaging agents, although fibrin and platelets already in an existing thrombus remain targets even in aged thrombi.

Attempts to provide radiotracers for imaging thrombi are known in the prior art. These include autologous platelets, labeled with either $^{111}$In or $^{99m}$Tc (Tc-99m), and $^{123}$- and $^{125}$I-labeled fibrinogen (the latter detected with a gamma scintillation probe as opposed to a gamma camera). In addition, other thrombus-associated components of the coagulation system, such as enzymes (e.g. thrombin), proenzymes and other factors may be useful as thrombus-associated targets for radiotracers. Additional radiolabeled compounds used to label thrombi include plasmin, plasminogen activators, heparin, fibronectin, fibrin Fragment $E_1$ and anti-fibrin and anti-platelet monoclonal antibodies [see Knight, 1990, Sem. Nucl. Med. 20: 52–67 for review].

Of the methods of radiolabeling thrombi known in the prior art, the methods that have shown the most promise are radiolabeled platelets, radiolabeled antibodies and radiolabeled fibrin Fragment $E_1$. All of these have serious drawbacks with regard to their routine use.

The use of radiolabeled autologous platelets to image thrombi requires that autologous blood be drawn, the platelets then separated and radiolabeled under sterile conditions [in addition, radiolabeling must be performed so as to avoid activating the platelets], and the radiolabeled platelets then be readministered to the patient. Such radiolabeled platelets have a long circulating time, resulting in poor target to non-target ratios at early times, thereby requiring that radioimaging be performed only after a delay of 24 to 72 hours. Moreover, aged thrombi are poorly visualized since such thrombi do not efficiently incorporate fresh platelets.

Radiolabeled antifibrin and antiplatelet monoclonal antibodies have also been used in the prior art (typically to image DVT). The disadvantage to using such reagents is that antibodies (and even antibody fragments) have slow blood and general tissue clearance characteristics and require a delay of at least several hours for optimum imaging. In addition, immunological reagents have the capacity to induce an immune response in the patient. Further, such reagents must be prepared from mammalian cell lines (hybridomas) and thus carry the risk of contamination by infectious human viruses.

Methods of using large radiolabeled peptides for imaging thrombi have been described in the prior art. For example, Fragment $E_1$ is a peptide derived from coagulated, cross-linked fibrin. It has been labeled with $^{123}I$ and Tc-99m to provide high quality images in humans.

Olexa et al., 1982, European Patent Application No. 823017009 disclose a pharmaceutically acceptable radiolabeled peptide selected from Fragment $E_1$ isolated from cross-linked fibrin, Fragment $E_2$ isolated from cross-linked fibrin, and peptides having an amino acid sequence intermediate between Fragments $E_1$ and $E_2$. Unfortunately, this protein fragment must be laboriously prepared from human fibrinogen, making it unsuitable for routine manufacture.

Hadley et al., 1988, PCT/US88/03318 disclose a method for detecting a fibrin-platelet clot in vivo comprising the steps of (a) administering to a patient a labeled attenuated thrombolytic protein, wherein the label is selectively attached to a portion of the thrombolytic protein other than the fibrin binding domain; and (b) detecting the pattern of distribution of the labeled thrombolytic protein in the patient.

Sobel, 1989, PCT/US89/02656 discloses a method to locate the position of one or more thrombi in an animal using radiolabeled, enzymatically inactive tissue plasminogen activator.

Peptides having the ability to bind to thrombi are known in the prior art.

Ruoslahti & Pierschbacher, U.S. Pat. No. 4,578,079 describe peptides of sequence X-Arg-Gly-Asp-Y, wherein X and Y are either H or an amino acid, and R is Thr or Cys, the peptides capable of binding to thrombi in vivo.

Ruoslahti & Pierschbacher, U.S. Pat. No. 4,792,525 describe peptides of sequence Arg-Gly-Asp-X, wherein X is Ser, Thr or Cys, the peptides capable of binding to thrombi in vivo.

Hawiger et al., 1989, PCT/US89/01742 relates to peptides comprising sequences for two binding sites of a protein.

Barker et al., 1991, PCT/US90/03788 disclose cyclic peptides for inhibiting platelet aggregation.

Radiolabeled peptides useful for radioimaging thrombi have been reported in the prior art.

Ranby et al., 1988, PCT/US88/02276 disclose a method for detecting fibrin deposits in an animal comprising covalently binding a radiolabeled compound to fibrin.

Stuttle, 1990, PCT/GB90/00933 discloses radioactively labeled peptides containing from 3 to 10 amino acids comprising the sequence arginine-glycine-aspartic acid (RGD), capable of binding to an RGD binding site in vivo.

Rodwell et al., 1991, PCT/US91/03116 disclose conjugates of "molecular recognition units" with "effector domains".

Maraganore et al., 1991, PCT/US90/04642 disclose a radiolabeled thrombus inhibitor comprising (a) a inhibitor moiety; (b) a linker moiety; and (c) and an "anion binding exosite (ABE)" binding site moiety.

The use of chelating agents for radiolabeling polypeptides, and methods for labeling peptides and polypeptides with Tc-99m are known in the prior art and are disclosed in co-pending U.S. patent applications Ser. Nos. U.S. Ser. No. 07/653,012, now abandoned, which has been allowed as U.S. Ser. No. 08/480,551; U.S. Ser. No. 07/807,062, now U.S. Pat. No. 5,443,815; and U.S. Ser. No. 07/851,074, now abandoned, which issued as U.S. Pat. No. 5,711,931 which are hereby incorporated by reference.

There remains a need for a small (to enhance blood and background tissue clearance), synthetic (to make routine manufacture practicable and to ease regulatory acceptance) molecules radiolabeled with Tc-99m for use in imaging thrombi in vivo. Small synthetic peptides radiolabeled with Tc-99m that bind specifically to components of thrombi fulfill this need and are provided by this invention.

SUMMARY OF THE INVENTION

The present invention provides scintigraphic imaging agents that are radioactively-labeled peptide reagents. Specifically, the invention provides peptide reagents for preparing thrombus imaging agents that are technetium-99m (Tc-99m) labeled. Thrombus imaging agents of the invention are comprised of a specific binding peptide that specifically binds to a thrombus in vivo that is covalently linked to a Tc-99m binding moiety and labeled with Tc-99m.

In a first aspect of the present invention, the invention provides peptide reagents capable of being Tc-99m labeled for imaging thrombus sites within a mammalian body, comprising a specific binding peptide having an amino acid sequence of 4–100 amino acids covalently linked to a Tc-99m binding moiety of formula:

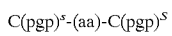

$$C(pgp)^s\text{-}(aa)\text{-}C(pgp)^s$$

wherein $C(pgp)^s$ is a protected cysteine and (aa) is an amino acid. In a preferred embodiment, the amino acid is glycine. In a preferred embodiment, the peptide comprises between 4 and 30 amino acids.

In a second embodiment, the invention provides peptide reagents capable of being Tc-99m labeled for imaging thrombus sites within a mammalian body, comprising a specific binding peptide having an amino acid sequence of 4–100 amino acids covalently linked to a Tc-99m binding moiety of formula:

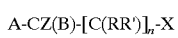

$$A\text{-}CZ(B)\text{-}[C(RR')]_n\text{-}X$$

wherein

A is H, HOOC, H$_2$NOC, or —NHOC;
B is SH or NHR";
X is H, methyl, SH or NHR";
Z is H or methyl;
R and R' are independently H or lower alkyl;
R" is H, lower alkyl or —C=O;
n is 0, 1 or 2;
and where B is NHR", X is SH, Z is H and n is 1 or 2; where X is NHR", B is SH, Z is H and n is 1 or 2; where B is H, A is HOOC, H$_2$NOC, or —NHOC, X is SH, Z is H and n is 0 or 1; where Z is methyl, X is methyl, A is HOOC, H$_2$NOC, or NHOC, B is SH and n is 0; and wherein the thiol moiety is in the reduced form. In a preferred embodiment, the peptide comprises between 4 and 30 amino acids.

In another embodiment, the invention provides peptide reagents capable of being labeled with Tc-99m for imaging thrombus sites within a mammalian body, comprising a specific binding peptide having an amino acid sequence of 4–100 amino acids covalently linked to a Tc-99m binding moiety of formula:

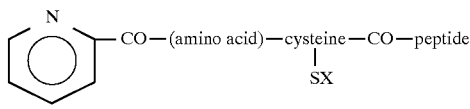

[for purposes of this invention, radiolabel-binding moieties having this structure will be referred to as picolinic acid (Pic)-based moieties]
or

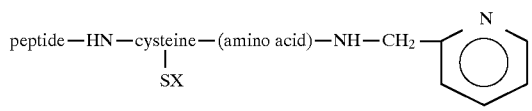

wherein X is H or a protecting group; (amino acid) is any amino acid and the radiolabel-binding moiety is covalently linked to the peptide. For purposes of this invention, radiolabel-binding moieties having this structure will be referred to as picolylamine (Pica)-based moieties. In a preferred embodiment, the amino acid is glycine and X is an acetamidomethyl protecting group. In additional preferred embodiments, the peptide is comprises between 4 and 30 amino acids.

Yet another embodiment of the invention provides peptide reagents capable of being labeled with Tc-99m for imaging thrombus sites within a mammalian body, comprising a specific binding peptide having an amino acid sequence of 4–100 amino acids covalently linked to a Tc-99m binding moiety that is a bisamino bisthiol Tc-99m binding moiety. The bisamino bisthiol Tc-99m binding moiety in this embodiment of the invention has a formula selected from the group consisting of:

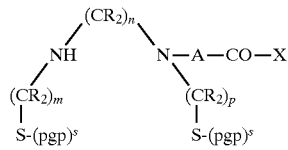

I.

wherein each R can be independently H, CH$_3$ or C$_2$H$_5$; each (pgp)$^s$ can be independently a thiol protecting group or H; m, n and p are independently 2 or 3; A is linear or cyclic lower alkyl, aryl, heterocyclyl, combinations or substituted derivatives thereof; and X is peptide; and

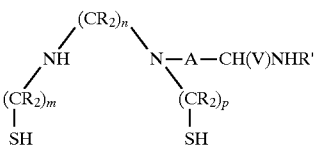

II.

wherein each R is independently H, CH$_3$ or C$_2$H$_5$; m, n and p are independently 2 or 3; A is linear or cyclic lower alkyl, aryl, heterocyclyl, combinations or substituted derivatives thereof; V is H or CO-peptide; R' is H or peptide; provided that when V is H, R' is peptide and when R' is H, V is peptide. For purposes of this invention, radiolabel-binding moieties having these structures will be referred to as "BAT" moieties. In a preferred embodiment, the peptide is comprised between 4 and 30 amino acids.

The invention also provides thrombus imaging agents for imaging a thrombus within a mammalian body comprising a specific binding peptide having an amino acid sequence of 4 to 100 amino acids and a technetium-99m binding moiety covalently linked to the specific binding peptide, wherein the peptide is selected from the group consisting of linear and cyclic peptides that are ligands for a GPIIb/IbIa receptor and do not comprise the amino acid sequence (arginine-glycine-aspartate), peptides that are ligands for a polymerization site of fibrin, and cyclic peptides comprising the amino acid sequence (arginine-glycine-aspartate). In a preferred embodiment, the amino acid sequence of peptides that are ligands for a polymerization site of fibrin comprise multiple copies of the sequence (glycyl-prolyl-arginyl-prolyl).

The invention also comprises scintigraphic imaging agents that are complexes of the peptide reagents of the invention with Tc-99m and methods for radiolabeling the peptide reagents of the invention with Tc-99m. Radiolabeled complexes provided by the invention are formed by reacting the peptide reagents of the invention with Tc-99m in the presence of a reducing agent. Preferred reducing agents include but are not limited to dithionite ion, stannous ion and ferrous ion. Complexes of the invention are also formed by labeling the peptide reagents of the invention with Tc-99m by ligand exchange of a prereduced Tc-99m complex as provided herein.

The invention also provides kits for preparing scintigraphic imaging agents that are the peptide reagents of the invention radiolabeled with Tc-99m. Kits for labeling the peptide reagents of the invention with Tc-99m are comprised of a sealed vial containing a predetermined quantity of a peptide reagent of the invention and a sufficient amount of reducing agent to label the peptide with Tc-99m.

This invention provides methods for preparing peptide reagents of the invention by chemical synthesis in vitro. In a preferred embodiment, peptides are synthesized by solid phase peptide synthesis.

This invention provides methods for using scintigraphic imaging agents that are Tc-99m labeled peptide reagents for imaging a thrombus within a mammalian body by obtaining in vivo gamma scintigraphic images. These methods comprise administering an effective diagnostic amount of Tc-99m labeled peptide reagents of the invention and detecting the gamma radiation emitted by the Tc-99m label localized at the thrombus site within the mammalian body.

Specific preferred embodiments of the present invention will become evident from the following more detailed description of certain preferred embodiments and the claims.

DETAILED DESCRIPTION OF THE INVENTION

The present invention provides peptide reagents for preparing radiolabeled thrombus imaging agents for imaging a thrombus within a mammalian body comprising an amino acid sequence covalently linked to a technetium-99m binding moiety. For purposes of the invention, the term thrombus imaging reagent will refer to embodiments of the invention comprising a specific binding peptide covalently linked to a Tc-99m binding moiety and labeled with Tc-99m.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

In the Tc-99m binding moieties and peptides covalently linked to such moieties that contain a thiol covalently linked to a thiol protecting groups $[(pgp)^s]$ provided by the invention, the thiol-protecting groups may be the same or different and may be but are not limited to:

- —CH$_2$-aryl (aryl is phenyl or alkyl or alkyloxy substituted phenyl);
- —CH—(aryl)$_2$, (aryl is phenyl or alkyl or alkyloxy substituted phenyl);
- —C—(aryl)$_3$, (aryl is phenyl or alkyl or alkyloxy substituted phenyl);
- —CH$_2$-(4-methoxyphenyl);
- —CH—(4-pyridyl)(phenyl)$_2$;
- —C(CH$_3$)$_3$
- -9-phenylfluorenyl;
- —CH$_2$NHCOR (R is unsubstituted or substituted alkyl or aryl);
- —CH$_2$—NHCOOR (R is unsubstituted or substituted alkyl or aryl);
- —CONHR (R is unsubstituted or substituted alkyl or aryl);
- —CH$_2$—S—CH$_2$-phenyl Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

Each specific-binding peptide provided by the invention is comprised of a sequence of amino acids. The term amino acid as used in this invention is intended to include all L- and D- amino acids, naturally occurring and otherwise. Specific-binding peptides provided by the invention include but are not limited to peptides having the following sequences:

Ligands for the GPIIb/IIIa Receptor

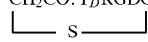
CH$_2$CO.Y$_D$RGDC (SEQ. ID NO.1)

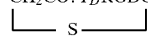
CH$_2$CO.Y$_D$RGDCWGG (SEQ. ID NO.2)

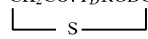
CH$_2$CO.Y$_D$RGDCFG (SEQ. ID NO.3)

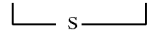
CH$_2$CO.Y$_D$RGDCGGG (SEQ. ID NO.4)

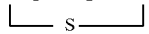
CH$_2$CO.Y$_D$RGDCGG (SEQ. ID NO.5)

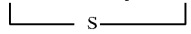
CH$_2$CO.Y$_D$.Apc.GDCGGG (SEQ. ID NO.6)

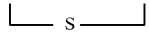
CH$_2$CO.Y$_D$KGDCGGG (SEQ. ID NO.7)

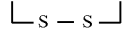
GGCNP.Apc.GDC (SEQ. ID NO.8)

GGRGDS (SEQ. ID NO. 9)
GGRGDGGRGDS (SEQ. ID NO. 10)
GGRGDGGRGDGGRGDS (SEQ. ID NO. 11)
KRARGDDMDDY (SEQ. ID NO. 12)
RRRRRRRRRGD (SEQ. ID NO. 13)
GRGDVK (SEQ. ID NO. 14)
GRGDV (SEQ. ID NO. 15)
GRGDVRGDFK (SEQ. ID NO. 16)
GRGDVRGDF (SEQ. ID NO. 17)
GGGRGDF (SEQ. ID NO. 18)
NP.Apc.GD (SEQ. ID NO. 19)
RGD
GRGDGG (SEQ. ID NO. 20)
GGRGDF (SEQ. ID NO. 21)
GGRGDF (SEQ. ID NO. 22)
GRGDGGGG (SEQ. ID NO. 23)
GRGDGG (SEQ. ID NO. 24)
GGRGDF (SEQ. ID NO. 25)
GGGRGDF (SEQ. ID NO. 26)
RGDF
G.Apc.GDV.Apc.GDFKamide (SEQ. ID NO. 27)
[SYNRGDSTC(S-maleimido)CH$_2$CH$_2$-]$_3$N (SEQ. ID NO. 28)

Thrombin Ligands
NDGDFEEIPEEYLQ (SEQ. ID NO. 29)
GGF$_D$PRPGGGGNGDFEEIPEEYL (SEQ. ID NO. 30)
GGGF$_D$PRPGGGGNGDFEEIPEEYL (SEQ. ID NO. 31)
GGF$_D$PRPGamide (SEQ. ID NO. 32)

Ligands for Polymerizing Fibrin
[GPRPC$_{Acm}$GC$_{Acm}$C(S-maleimido)CH$_2$CH$_2$-]$_3$N (SEQ. ID NO. 33)
[(GPRP)$_2$K]$_2$K
(GPRVVERHQSA)$_2$K Specific-binding peptides of the present invention can be chemically synthesized in vitro. Peptides of the present invention can generally advantageously be prepared on an amino acid synthesizer. The peptides of this invention can be synthesized wherein the radiolabel-binding moiety is covalently linked to the peptide during chemical synthesis in vitro, using techniques well known to those with skiU in the art. Such peptides covalently-linked to the radiolabel-binding moiety during synthesis are advantageous because specific sites of covalent linkage can be determined.

Radiolabel binding moieties of the invention may be introduced into the target specific peptide during peptide synthesis. For embodiments comprising picolinic acid [(Pic-); e.g., Pic-Gly-Cys(protecting group)-], the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic-Gly-Cys- and -Cys-Gly-Pica chelators are provided in the Examples hereinbelow. This invention provides for the incorporation of these chelators into virtually any peptide capable of specifically binding to a thrombus in vivo, resulting in a radiolabeled peptide having Tc-99m held as neutral complex.

This invention also provides specific-binding small synthetic peptides which incorporate bisamine bisthiol (BAT) chelators which may be labeled with Tc-99m. This invention provides for the incorporation of these chelators into virtually any peptide capable of specifically binding to a thrombus in vivo, resulting in a radiolabeled peptide having Tc-99m held as neutral complex. An example of a small synthetic peptide containing a BAT chelator as radiolabel-binding moiety is provided in the example hereinbelow.

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

In a preferred embodiment of the invention, a kit for preparing technetium-labeled peptides is provided. An appropriate amount of the peptide reagent is introduced into a vial containing a reducing agent, such as stannous chloride, in an amount sufficient to label the peptide with Tc-99m. An appropriate amount of a transfer ligand as described (such as tartrate, citrate, gluconate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Radiolabeled thrombus imaging reagents according to the present invention may be prepared by the addition of an appropriate amount of Tc-99m or Tc-99m complex into the vials and reaction under conditions described in Example 2 hereinbelow.

Radioactively-labeled scintigraphic imaging agents provided by the present invention are provided having a suitable amount of radioactivity. In forming Tc-99m radioactive complexes, it is generally preferred to form radioactive complexes in solutions containing radioactivity at concentrations of from about 0.01 millicurie (mCi) to 100 mCi per mL.

The thrombus imaging reagents provided by the present invention can be used for visualizing thrombi in a mammalian body when Tc-99m labeled. In accordance with this invention, the Tc-99m labeled peptide reagents are administered in a single unit injectable dose. The Tc-99m labeled peptide reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging of the thrombus in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxybenzotriazole (HBTU/HOBT), and using p-hydroxymethylphenoxymethyl-polystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature.

Where appropriate, N-terminal acetyl groups were introduced by treating the free N-terminal amino peptide bound to the resin with 20% v/v acetic anhydride in NMP (N-methylpyrrolidinone) for 30 min. Where appropriate, 2-chloroacetyl and 2-bromoacetyl groups were introduced either by using the appropriate 2-halo-acetic acid as the last residue to be coupled during SPPS or by treating the N-terminus free amino peptide bound to the resin with either the 2-halo-acetic acid/diisopropylcarbodiimide/N-hydroxysuccinimide in NMP of the 2-halo-acetic anhydride/ diisopropylethylamine in NMP. Where appropriate, HPLC-purified 2-haloacetylated peptides were cyclized by stirring an 0.1–1.0 mg/mL solution in phosphate or bicarbonate buffer (pH 8) containing 0.5–1.0 mM EDTA for 4–48 hours, followed by acidification with acetic acid, lyophilization and HPLC purification. Where appropriate, Cys—Cys disulfide bond cyclizations were performed by treating the precursor cysteine-free thiol peptides at 0.1 mg/mL in pH 7 buffer with aliquots of 0.006 M $K_3Fe(CN)_6$ until a stable yellow color persisted. The excess oxidant was reduced with excess cysteine, the mixture was lyophilized and then purified by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

EXAMPLE 2

A General Method for Radiolabeling with Tc-99m 0.1 mg of a peptide prepared as in Example 2 was dissolved in 0.1 mL of water or 50 mM potassium phosphate buffer (pH=5, 6 or 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 $\mu$l of Tc-99m gluceptate was then added to the peptide and the reaction allowed to proceed at room temperature or at 100° C. for 15–30 min and then filtered through a 0.2 $\mu$m filter.

The Tc-99m labeled peptide purity was determined by HPLC using the conditions described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 2 using the method described herein.

| Peptides | FABMS MH+ | Radiochemical Yield (%)* | HPLC $R_T$ (min)** |
|---|---|---|---|
| $CH_2CO.Y_DRGDCC_{Acm}GC_{Acm}$amide (S—S) | 1057 | 97[2] | 10.0, 10.4, 10.6[2] |
| $CH_2CO.Y_DRGDCWGGC_{Acm}GC_{Acm}$amide (S—S) | 1357 | 100[4] | 15.9, 16.4[2] |
| $CH_2CO.Y_DRGDCFGGC_{Acm}GC_{Acm}$amide (S—S) | 1318 | 97[4] | 15.9, 16.3[2] |
| $CH_2CO.Y_DRGDCGGGC_{Acm}GC_{Acm}$amide (S—S) | 1310 | 99[2] | 11.8[2] |
| $CH_2CO.Y_DRGDCGGC_{Acm}GC_{Acm}$amide (S—S) | 1171 | 99[2] | 13.5[2] |
| $CH_2CO.Y_D.Apc.GDCGGGC_{Acm}GC_{Acm}$amide (S—S) | 1233 | 100[4] | 17.1, 18.1[2] |
| $CH_2CO.Y_DKGDCGGGC_{Acm}GC_{Acm}$amide (S—S) | 1200 | 96[4] | 15.8, 16.1[2] |
| $Pic.GC_{Acm}GGCNP.Apc.GDC$ (S—S) | 1217 | 70[2] | 6.6–13.7[2] |
| $Ac.C_{Acm}GC_{Acm}GGCNP.Apc.GDC$ (S—S) | 1327 | 98[2] | 13.0–15.5[2] |
| Ac.CNP.Apc.GDC | 832 | 99[1] | 12.9[2] |
| $C_{Acm}GC_{Acm}$GGRGDS | 953 | 100[2] | 8.6[1] |
| $C_{Acm}GC_{Acm}$GGRGDGGRGDS | 1396 | 100[1] | 12.6[1] |
| $C_{Acm}GC_{Acm}$GGRGDGGRGDGGRGDS | 1838 | 100[2] | 10.0, 10.8[1] |
| $C_{Acm}GC_{Acm}$RRRRRRRRRGD | 2100 | 100[2] | 2.4[3]*** |
| $GRGDVKC_{Acm}GC_{Acm}$amide | 1036 | 100[2] | 15.7[2] |
| $GRGDVC_{Acm}GC_{Acm}$amide | 907 | 100[2] | 16.1[2] |
| $GRGDVRGDFKC_{Acm}GC_{Acm}$amide | 1510 | 97[2] | 16.2, 16.8[2] |
| $GRGDVRGDFC_{Acm}GC_{Acm}$amide | 1382 | 94[2] | 16.4[2] |
| $(GPRVVERHQSA)_2K$ | 2986 | 99[4] | 16.0[2] |
| CRGDC | 553 | 100[3] | 16.7[2] |
| GRGDGGC | 769 | 98[1] | 13.0, 13.6, 14.7[2] |
| maGGRGDF | 739 | 98[1] | 13.8–14.7[2] |
| mmpGGGRGDF | 767 | 100[3] | 18.4, 19.3[2] |

-continued

| | | | |
|---|---|---|---|
| GRGDGGGGC | 735 | 100[3] | 14.9, 15.1, 15.4[3] |
| maRGD | 421 | 97[3] | 16.1, 16.9, 17.7[2] |
| maRGDF | 568 | 94[3] | 18.1, 18.7[2] |
| CKRARGDDMDDYC | 1548 | 97[3] | 16.7[2] |
| [Pic.SC$_{Acm}$SYNRGDSTC(S-maleimido)CH$_2$CH$_2$—]$_3$N[a] | 4489 | 99[2] | 10.4, 11.2[2] |
| C$_{Acm}$GC$_{Acm}$NDGDFEEIPEEYLQ | 2103 | 100[2] | 2.5[1]*** |
| C$_{Acm}$GC$_{Acm}$GGF$_D$PRPGGGGNGDFEEIPEEYL | 2699 | 99[2] | 14.5[3] |
| maGGGF$_D$PRPGGGGNGDFEEIPEEYL | 2426 | 95[2] | 17.4[2] |
| C$_{Acm}$GC$_{Acm}$GGF$_D$PRPGamide | 1092 | 100[5] | 9.6[2] |
| [GPRPC$_{Acm}$GC$_{Acm}$C(S-maleimido)CH$_2$CH$_2$—]$_3$N[b] | 3189 | 93[2] | 10.0[2] |
| [(GPRP)$_2$K]$_2$KC$_{Acm}$GC$_{Acm}$amide | 2437 | 100[4] | 16.3[2] |
| [BAT]G.Apc.GDV.Apc.GDFKamide | 1432 | 96[3] | 17.5[2] |

*Superscripts refer to the following labeling conditions:
1. The peptide is dissolved in 50 mM potassium phosphate buffer (pH 7.4) and labeled at room temperature.
2. The peptide is dissolved in 50 mM potassium phosphate buffer (pH 7.4) and labeled at 100° C.
3. The peptide is dissolved in water and labeled at room temperature.
4. The peptide is dissolved in water and labeled at 100° C.
5. The peptide is dissolved in 50 mM potassium phosphate buffer (pH 6.0) and labeled at 100° C.
6. The peptide is dissolved in 50 mM potassium phosphate buffer (pH 5.0) and labeled at room temperature.

**HPLC methods (indicated by superscript after $R_T$):
general: solvent A = 0.1% CF$_3$COOH/H$_2$O
solvent B$_{70}$ = 0.1% CF$_3$COOH/70% CH$_3$CN/H$_2$O
solvent B$_{90}$ = 0.1% CF$_3$COOH/90% CH$_3$CN/H$_2$O
solvent flow rate = 1 mL/min
Vydak column = Vydak 218TP54 RP-18, 5$\mu$ × 220 mm × 4.6 mm analytical column with guard column
Brownlee column = Brownlee Spheri-5 RP-18, 5$\mu$ × 220 mm × 4.6 mm column
Method 1: Brownlee column 100% A to 100% B$_{70}$ in 10 min
Method 2: Vydak column 100% A to 100% B$_{90}$ in 10 min
Method 3: Vydak column 100% A to 100% B$_{70}$ in 10 min
***Confirmed by sodium dodecyl sulfate-polyacrylamide gel electrophoresis
****Confirmed by binding the peptide to an affinity column
Single-letter abbreviations for amino acids can be found in G. Zubay, Biochemistry (2d. ed.), 1988 (MacMillen Publishing: New York) p. 33; Ac = acetyl; Pic = picolinoyl (pyridine-2-carbonyl); Acm = acetamidomethyl; Mob = 4-methoxybenzyl; Apc = L-[S-(3-aminopropyl)cysteine];
F$_D$ = D-phenylalaine; Y$_D$ = D-tyrosine; Cpa = L-(4-chlorophenyl)alanine;
ma = 2-mercaptoacetic acid; mmp = 2-mercapto-2-methylpropionic acid;
BAT = HSC(CH$_3$)$_2$CH$_2$NHCH$_2$CH$_2$N(CH$_2$CH$_2$CH$_2$CH$_2$CO—)CH$_2$C(CH$_3$)$_2$SH
[a]The structure of this compound is as follows:

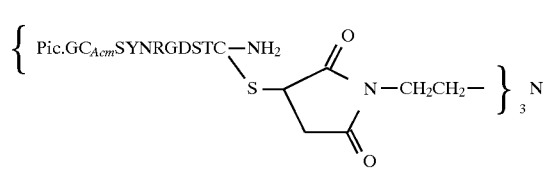

[b]The structure of this compound is as follows:

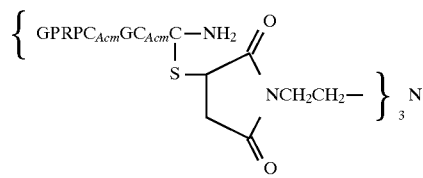

It should be understood that the foregoing disclosure emphasizes certain specific embodiments of the invention and that all modifications or alternatives equivalent thereto are within the spirit and scope of the invention as set forth in the appended claims.

What is claimed is:

1. A reagent for preparing a thrombus imaging agent comprising a specific binding peptide having an amino acid sequence of 4 to 100 amino acids and a technetium-99m binding moiety covalently linked to the peptide, wherein the peptide is selected from the group consisting of a cyclic peptide ligand for a GPIIb/IIIa receptor and a linear peptide ligand for the GPIIb/IIIa receptor not comprising the amino acid sequence (arginine-glycine-aspartate).

2. A composition comprising a peptide having a formula selected from the group consisting of:

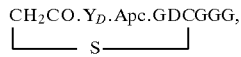

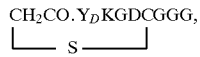

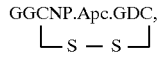

NP.Apc.Gd; and
G.Apc.GDV.Apc.GDFKamide.

3. The reagent according to claim 1, wherein the peptide and the technetium-99m binding moiety are covalently linked through one or more amino acids.

4. A composition of matter comprising the reagent according to claim 1 and a stannous ion.

5. A kit for preparing a radiopharmaceutical preparation, said kit comprising a sealed vial containing a predetermined quantity of a reagent according to claim 1 and a sufficient amount of a reducing agent to label said reagent with technetium-99m.

6. The reagent according to claim 1, wherein the peptide is chemically synthesized in vitro.

7. The reagent according to claim 6, wherein the peptide is synthesized by solid phase peptide synthesis.

8. The reagent according to claim 6 wherein the technetium-99m binding moiety is covalently linked to the peptide during in vitro chemical synthesis.

9. The reagent according to claim 8 wherein the technetium-99m binding moiety is covalently linked to the peptide during solid phase peptide synthesis.

10. The reagent of claim 1, wherein the peptide is selected from the group consisting of:

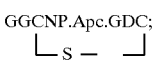

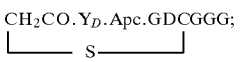

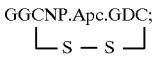

NP.Apc.GD;

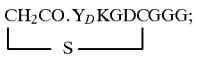

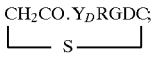

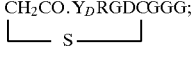

$CH_2CO.Y_DRGDCGG.$
|— S ———|

* * * * *